United States Patent [19]
Koger et al.

[11] Patent Number: 5,454,373
[45] Date of Patent: Oct. 3, 1995

[54] MEDICAL ACOUSTIC IMAGING

[75] Inventors: James D. Koger, Cambridge; Robert J. Crowley, Wayland; Jean C. Vincent, Bradford; Peter M. Nicholas, South Dartmouth, all of Mass.

[73] Assignee: Boston Scientific Corporation, Natick, Mass.

[21] Appl. No.: 278,079

[22] Filed: Jul. 20, 1994

[51] Int. Cl.[6] .................................................. A61B 8/12
[52] U.S. Cl. ............................................. 128/662.06
[58] Field of Search ...................... 128/662.03, 660.02, 128/662.05, 662.06, 663.01, 660.09, 660.10, 772

[56] References Cited

U.S. PATENT DOCUMENTS

| | | | |
|---|---|---|---|
| 4,899,757 | 2/1990 | Pope, Jr. et al. | 128/662.06 |
| 5,039,774 | 8/1991 | Shikinami et al. | 128/660.02 |
| 5,090,414 | 2/1992 | Takano | 128/662.06 |
| 5,091,205 | 2/1992 | Fan | 427/2 |
| 5,115,814 | 5/1992 | Griffith et al. | 28/662.06 |
| 5,135,516 | 8/1992 | Sahatjian et al. | 604/265 |
| 5,166,073 | 11/1992 | Lefkowitz et al. | 128/662.06 |
| 5,304,121 | 4/1994 | Sahatjian | 604/53 |
| 5,305,755 | 4/1994 | Nakao | 128/662.06 |
| 5,368,035 | 11/1994 | Hamm et al. | 128/662.06 |
| 5,372,138 | 12/1994 | Crowley et al. | 128/662.06 |
| 5,375,601 | 12/1994 | Nicholas et al. | 128/662.06 |

FOREIGN PATENT DOCUMENTS

| | | | |
|---|---|---|---|
| WO92/03095 | 3/1992 | WIPO | A61B/8/12 |
| WO93/16642 | 9/1993 | WIPO | A61B/8/12 |

OTHER PUBLICATIONS

Bom et al., "Early and Present Exmaples of Intraluminal Ultrasonic Echography," SPIE vol. 1068 Catheter–Based Sensing and Imaging Technology, 1989, pp. 146–150.

Gichard et al., "Development of a Mechanically Scanned Doppler Blood Flow Catheter," 1975 Ultrasonics Symposium Proceedings, IEEE Cat. #75 CHO 994–4SU, pp. 18–21.

*Primary Examiner*—George Manuel
*Attorney, Agent, or Firm*—Fish & Richardson

[57] ABSTRACT

An ultrasound imaging device has a stationary, elongated flexible tubular body, a rotatable drive shaft extending through the body, and a nose member located distally of the tubular body. The nose member is mounted on the distal end of the drive shaft to rotate therewith, and an acoustic imaging instrument is incorporated in the nose member for producing acoustic images of adjacent tissue as the drive shaft turns. The nose member is covered with a bio-compatible, acoustically transparent, lubricous coating of hydrophilic material sufficient to shield and space the nose member from the adjacent tissue. The lubricous coating of hydrophilic material covers an area of the surface of the ultrasound imaging device through which the acoustic imaging instrument causes acoustic signals to pass. The coating has sufficient thickness to avoid puncturing of a wall of a blood vessel by the nose member while the nose member rotates within the blood vessel sufficiently close to the wall for puncturing otherwise to occur.

33 Claims, 4 Drawing Sheets

MEDICAL ACOUSTIC IMAGING

BACKGROUND OF THE INVENTION

The present invention relates in general to acoustic imaging of regions within the body of a living being and more particularly concerns apparatus and techniques combining advantageous features typical of guidewires and ultrasound imaging probes.

Some of the features needed for a commercially practical design of such imaging devices are a construction that enables it to be conveniently made in a range of small sizes down to very small size, a distal end which can exert a degree of distal thrust to access parts of the body easily, and a tip which is non-traumatic so that it does not enter delicate linings of blood vessels or other ducts of the body.

It is also desirable for many such devices that their transducers not only be capable of high frequencies as used in existing ultrasound imaging catheters and guidewires but also for much higher frequencies, e.g. for closer imaging.

Ultrasonic imaging devices should also have usual guidewire-like qualities or catheter-like qualities, for instance variable stiffness along their length. A more flexible distal portion enables access to difficult-to-access regions of the body, while a stiffer proximal region of the catheter or guidewire enables pushing and manipulation. For instance, when imaging the coronary arteries, it is desirable to readily place a device in the femoral artery through a coronary guiding catheter, around the aortic arch and into the coronary ostium. Generally the guiding catheter only extends up to but not into the coronary ostium. With an appropriate design of an ultrasound device, with a very flexible distal portion, it becomes possible to exert good control over the imaging tip that is placed directly from the coronary ostium into the more distal region of the coronary artery.

It is also desirable to provide an ultrasound imaging device which is immediately usable rather than having to prepare a device specially by injection of water or saline or other fluid acoustic coupling medium.

It has been known to employ an acoustic imaging catheter which has the additional capability of fluid and drug delivery. It is desirable to achieve ways of doing this with improved or different versions of catheters that are produced to better fulfill the needs of physicians.

It has been known to apply thin lubricous coatings to guidewires and catheter devices to aid in deployment of the guidewire or catheter device and to protect bodily passages from abrasion during insertion and rotation of the guidewire or catheter device. Such thin lubricous coatings are described in Sahatjian et al., U.S. Pat. No. 5,135,516 and Sahatjian, U.S. Pat. No. 5,304,121, the entire disclosures of which are hereby incorporated by reference herein.

With prior designs, it has not been feasible to achieve all desirable combinations of the above features.

SUMMARY OF THE INVENTION

According to one aspect of the invention, an ultrasound imaging device has a stationary, elongated flexible tubular body, a rotatable drive shaft extending through the body, and a nose member located distally of the tubular body. The nose member is mounted on the distal end of the drive shaft to rotate therewith, and an acoustic imaging instrument is incorporated in the nose member for producing acoustic images of adjacent tissue as the drive shaft turns. The nose member is covered with a bio-compatible, acoustically transparent, lubricous coating of hydrophilic material sufficient to shield and space the nose member from the adjacent tissue. The coating has sufficient thickness to avoid puncturing of a wall of a blood vessel by the nose member while the nose member rotates within the blood vessel sufficiently close to the wall for puncturing otherwise to occur.

According to another aspect of the invention the lubricous coating of hydrophilic material covers an area of the surface of the ultrasound imaging device through which the acoustic imaging instrument causes acoustic signals to pass.

Numerous features, objects, and advantages of the invention will become apparent from the following detailed description when read in connection with the accompanying drawings.

DETAILED DESCRIPTION

Figure 1:
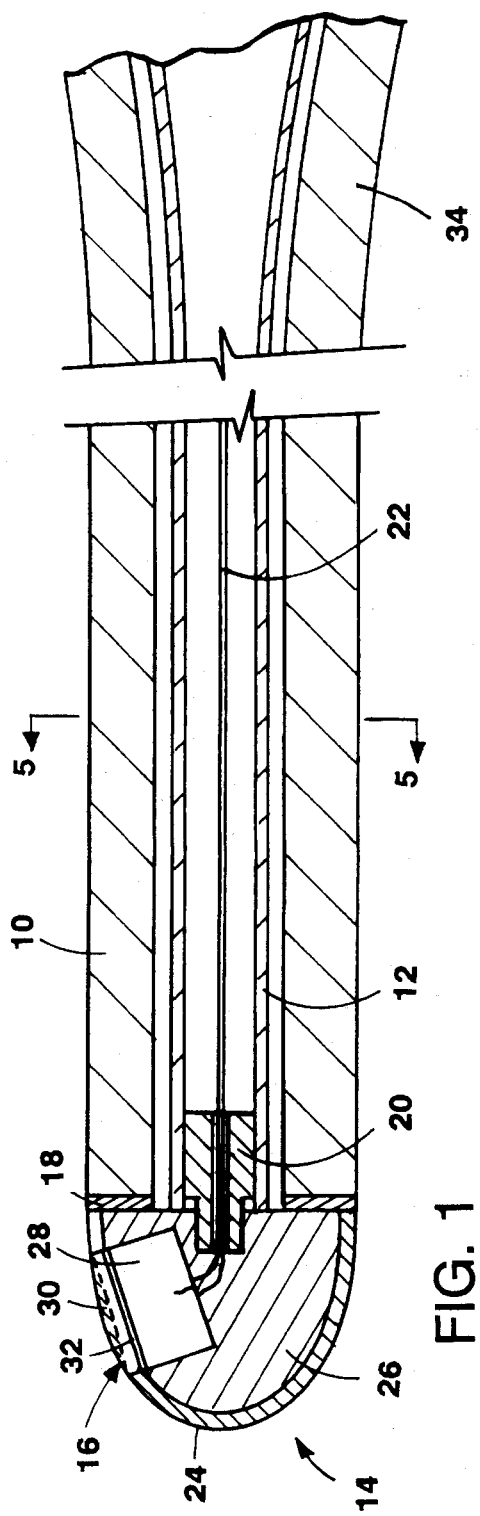
FIG. 1 shows a longitudinal cross-sectional view of the catheter or guidewire imaging device.

A preferred device has an elongated body 10 which houses rotary shaft 12 to which is attached transducer assembly 14 in which is mounted transducer 16. As a means for firmly attaching shaft 12 to the transducer assembly 14, a boss 20 is employed comprising a metallic plug which is press-fit into rotary shaft 12. Passing through boss 20 is wire 22 which extends from the conductive backing 28 of the transducer 16 and passes through shaft 12 to the proximal portion of the device. Transducer assembly 14 includes metal-epoxy filler 26 which forms a coherent, generally semi-spherical nose member which is coated with smooth epoxy coating 24. Transducer 16 comprises conductive backing 28, piezoelectric (PZT) layer 32 and conductive lens 30. For attaching transducer assembly 14 securely to shaft 12, boss 20 comprises a stepped hollow stainless steel bushing which is press-fit both into shaft 12 with an interference press fit and into the metal epoxy-filled transducer assembly.

As an alternative, the boss may be glued or otherwise bonded to the epoxy-filled assembly.

The transducer assembly 14 as shown has a generally hemispherical form. It may alternatively be blunt, a perfect hemisphere, or of slightly bullet-shaped elongated form, but in any case it provides a smooth, symmetric, atraumatic shape for exposure to body tissue and has a base diameter that substantially corresponds to the diameter of body 10. These parts are positioned close together to provide a uniform, atraumatic transition from moving end to stationary body without exposed sharp edges.

In use, transducer assembly 14 receives a degree of distal force as it passes into regions of the body and it receives lateral forces. To enable free rotation and yet prevent the transducer assembly 14 from changing its position relative to elongated body 10, end bearing 18 is provided. Bearing 18 is of flat annular form, made of TEFLON or stainless steel coated TEFLON, and is inserted between the proximal end of transducer assembly 14 and the distal end of body 10 to provide a low friction bearing surface that prevents galling of the surfaces and also limits lateral movement while still allowing rotation of transducer assembly 14 and shaft 12.

Figure 2:
FIG. 2 is a longitudinal cross-sectional view on an enlarged scale of the proximal end of the catheter or guidewire imaging device of FIG. 1 showing a male electrical connector.

Referring to FIG. 2, shaft 12 extends through elongated body 10 to beyond its proximal end. It is held in place by proximal thrust bearing 54 which is firmly attached to ring 36. Ring 36 also holds tip 38 and forms an electrical connector. The position of ring 36 creates a slight tension on shaft 12 (or, alternatively, compression in elongated body 10, or both) to maintain the position of transducer assembly 14 firmly on the ends of body 10.

Transducer 16 is a solid layered structure cut from a pre-formed slab. In forming a slab, conductive backing material 28 is first formed by mixing particles of tungsten or gold with an epoxy filler. Onto this backing is placed a layer 32 of ceramic material which is piezoelectric such as lead zirconate titinate, otherwise referred to as PZT. On top of the PZT layer 32 is formed another conductive layer of metal epoxy such as silver conductive epoxy, which forms a conductive lens 30. The pre-formed slab may be cut to form a small cube, rectangle or, as is presently preferred, cylinder.

The angle of the transducer 16 and transducer assembly 14 is tilted slightly forward to reduce specular reflection from nearby surfaces. The angle may be between five degrees and ten degrees for the purpose of reducing specular reflections. For a more forward look and to create a conical scan as might be desirable in imaging more distal regions of the anatomy, transducer 16 may be angled at a larger angle including nearly pointing forward, i.e. up to about 80 degrees forward.

Figure 6:
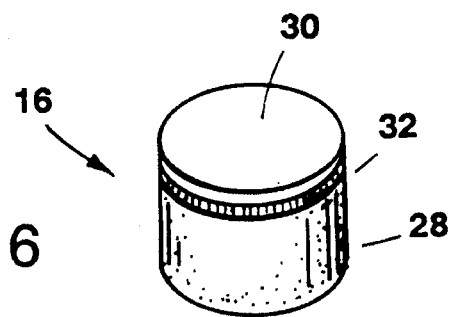
FIG. 6 is a perspective view of a transducer assembly formed from a slab to material.

Transducer 16 is shown in perspective view in detail in FIG. 6. It comprises a cylindrical plug of sandwiched material pre-formed prior to insertion. Lens 30 is the uppermost layer and may be either flat or concave for focusing. PZT layer 32 is generally flat, sandwiched between the two layers 28 and 30 while backing layer 28 comprises the bulk of the assembly, serving to absorb the acoustic backwave from PZT layer 32, allowing a short pulse to be produced, which is effective for close up imaging.

Transducer 16 is placed on one side of assembly 14.

To provide a smooth exterior surface, epoxy coat 24 is applied either by spraying or dipping, and then finally finished by grinding or polishing to provide an atraumatic smooth outer surface that can conduct ultrasound.

With such construction, the device is capable of imaging at frequencies that are similar to current intravascular ultrasound imaging practice, e.g., in the region from 8 to 30 MHz. The construction principles are also effective in the region of 30 to 300 MHz by virtue of the direct view of the surrounding tissue (i.e. without the need of the ultrasound to pass through a catheter wall or relatively thick window). Only a very thin epoxy coating layer, e.g. a thickness of one or a few thousandths of an inch or less may be employed for achieving the atraumatic surface over the transducer.

Figure 3:
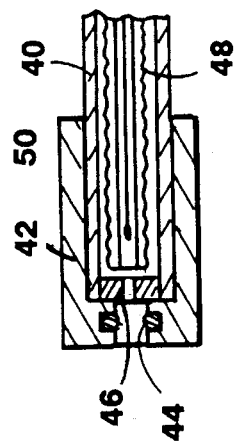
FIG. 3 is a longitudinal cross-sectional view of the same scale as FIG. 2 of a mating female connector which accepts the connector of FIG. 2.
Figure 4:
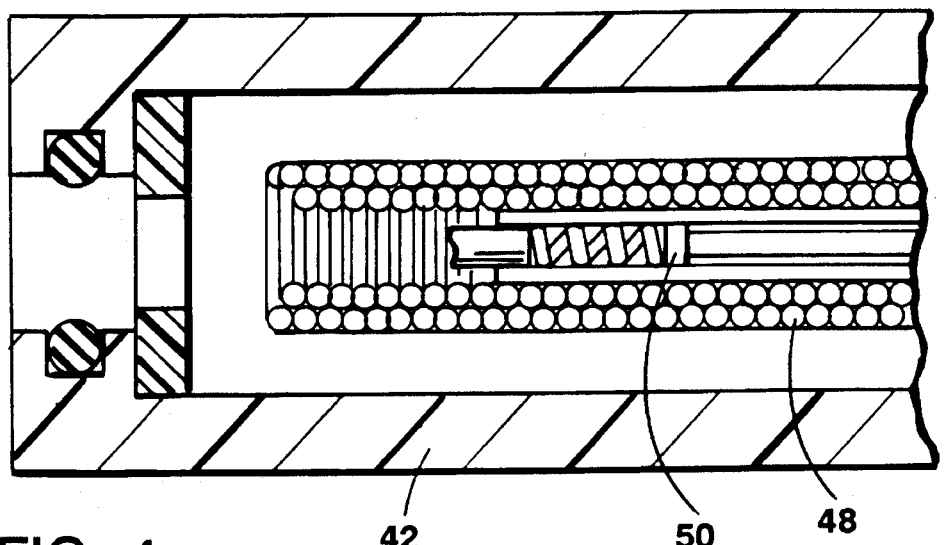
FIG. 4 is a longitudinal cross-sectional view on a considerably enlarged scale that shows the detail of a multifilar drive shaft and sliding pin arrangement for making electrical and mechanical contact simultaneously.
Figure 5:
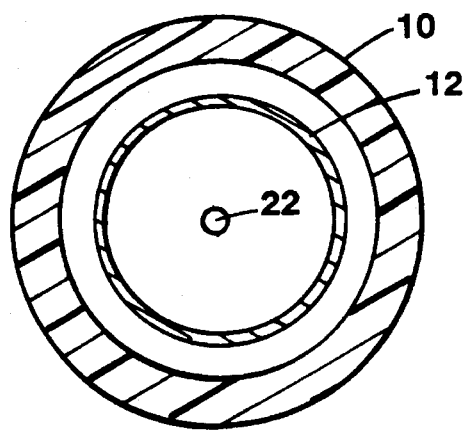
FIG. 5 is a transverse cross-sectional view of the distal portion of the device of FIG. 1 taken on line 55 of FIG. 1.

FIG. 3 shows a connector assembly for simultaneously making electrical and mechanical connection with the imaging guidewire or catheter assembly, linking the device to an ultrasound imaging console that has a motor driving circuit and electrical wires of commutation circuit. In FIG. 3, the proximal driver casing 40 is capped with proximal driver bushing 42. A tight fitting O-ring 44 is placed in the gland in proximal driver bushing 42. This creates an interfering state for body 10 when it is inserted into proximal driver bushing 42. In order to prevent the guidewire or catheter from being inserted too far, stop 46 is fixed inside of proximal driver bushing 42. To receive electrical connector, ring 36 and tip 38, a multifilar dual post drive shaft 48 (see FIG. 4) is modified with an open end so that it may accept the stub of tip 38 and ring 36 of the device in interfering fashion while making simultaneous electrical and rotary mechanical connection. For this purpose, a spring-center contact 50 is provided with a spring behind a sliding contact within multifilar drive shaft 48. The proximal end of the catheter-like or guidewire-like device is sized to fit into the drive shaft with interference when the proximal end of the device is inserted into proximal driver bushing 42. O ring 44 engages body 10 and holds the device securely in place while preventing bushing 54 from extending past stop 46.

When constructed for use as a catheter, the device is no larger than about 10 French and about 150 centimeters long. Such a device is useful for imaging portions of the heart. With such a construction a large transducer is employed capable of relatively deep penetration of heart tissue, using ultrasound frequencies in the range of about 8 MHz.

A smaller size catheter, of about 6 French and 150 centimeters length, is useful for imaging in the peripheral vessels, the chambers of the heart, the great arteries and veins, and also in other non-vascular ducts and ports of the body.

A smaller catheter size in the range of 4 French and about 150–175 centimeters length is useful for imaging the regions previously mentioned, and in addition, smaller arteries including possibly coronary arteries and arteries such as the carotid artery extending from the aortic arch, as well as in non-vascular regions.

A smaller size of about 3 French and 150–175 centimeters length is also useful for imaging mid-coronary arteries, distal coronary arteries and more distal regions of the carotid artery including the brain and the regions beyond the brain. A catheter of this size is also useful for imaging the tubular arteries and the distal extremities.

With all of these catheters just described, because there is no need for a relatively thick acoustic window to pass the ultrasound signal, acoustic loss is reduced that can limit penetration and resolution. Since window thickness produces attenuation and refraction which increases in proportion to frequency of operation, it follows that with the catheter-like and guidewire-like devices described above higher frequencies than 30 MHz may be successfully employed.

In fact, frequencies as high as 300 MHz are contemplated for very close-up imaging of the interior of blood vessels and arteries, veins, ducts and other areas of surrounding tissue where the device can be placed.

The ultrasound imaging device is contemplated to be particularly useful as a pre-assessment and post-assessment device with angioplasty. In angioplasty a balloon or a lesion-reducing means is inserted into the patient's artery and either a mechanical action or a rotary cutting action is used to change and open up or recanalyze the patient's artery. The present imaging device is used for passing into that region both before and after a procedure is conducted. The device is used to observe the nature of the stenosis, its extent, its diameter, its texture and also whether or not there are residual flaps, cracks, or other conditions which may cause problems later such as reocclusion or emboli.

Figure 1A:
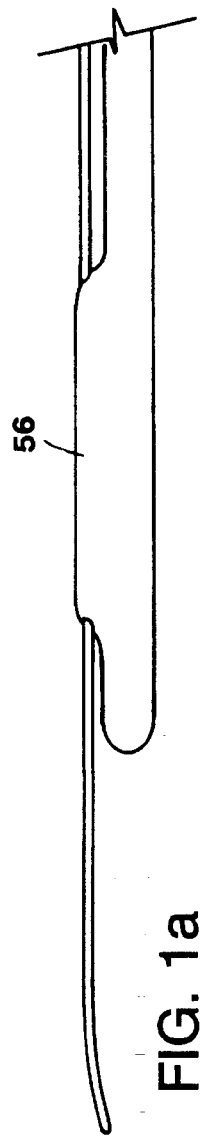
FIG. 1a is a side view of a catheter having a construction similar to that of FIG. 1, and having in addition, a saddle for introduction of the catheter over a guidewire.

Another ultrasound imaging device is shown in FIG. 1a. A catheter of the construction of FIG. 1 is provided with a "side saddle" 56. This feature is mounted along side and parallel to body 10 and is constructed to receive and ride upon a guidewire. It has a distal orifice positioned proximal to transducer assembly 14, and it continues along catheter body 10 for a distance of between a half centimeter and 75 centimeters, depending on the application, and has a proximal opening which allows the guidewire to exit.

This feature is useful for positioning the device within the peripheral vasculature, the iliac, the femoral, the aorta, the aortic arch, the heart, the distal extremities, the carotid artery and other blood vessels where a catheter with a side guidewire may be passed, or any other region of the body which has a duct, an orifice, or a tube in which a guidewire may first be placed and a catheter of this kind slid along the guidewire. There is also the possibility of using this guidewire-sided device in the coronary arteries.

Below 3 French in size, the device has guidewire-like properties. Guidewires tend to begin in the diameter range of 0.038 inches, extending down to as small as 0.10 inches.

An 0.035 inch diameter device constructed according to FIG. 1 can serve as an ultrasound imaging guidewire-type device, as there are many interventional accessories which have lumens which, for being guided into position, will slide over an 0.035 inch wire. A device of that size is contemplated to be useful by itself for imaging the coronary arteries (i.e. not serving as a guidewire). It also is contemplated as useful to serve as a guidewire for passing dilatation balloons used in the peripheral artery such as the ileac, the femorals and the aorta, or the umbiliary tree or in areas of the esophagus or the anus.

A device of 0.035 inch diameter may also be used to recanalyze or unblock arteries which are totally occluded that are sized approximately with an 0.035 inch guidewire. For an example, the femoral artery which is long may become totally occluded over a length of 2, 3 or even 20 centimeters. Frequently, this condition is treated by the application of a clot-dissolving enzyme such as urokinase, TpA or pro-urokinase over a period of time. This creates patient discomfort, is very expensive and time consuming, and one cannot tell when the job is done. An alternative to such treatment has been rotational recanalization using a slow rotation and thrusting motion of a rotating guidewire. Also lysing guidewires have been used, as reported in the medical literature.

We contemplate the present device can be used as a rotating drive shaft that is exposed to the blood or placed inside of a sheath, which slowly rotates and massages its way through the blocked artery either by separating or lysing (through a suitable drug delivery passage, not shown) or otherwise moving the blood clot or tissue out of the way to recanalyze the blood vessel. The ultrasound imaging device can thus be used to create a distal thrusting force and a slow rotational force to create an outward force that separates the tissue and finds its way through the lumen.

It is recognized that imaging of tissue in direct contact with the transducer 16 is not desirable because solid reflecting tissue in contact with acoustic imaging transducers harms image quality and creates image clutter which makes it difficult to visualize the scene.

However, we contemplate to use the device in the following manner. First it is used to thrust forward and recanalyze the artery. Then it is backed off to allow blood to fill the space that is created. Then the device is used to image the region of the body that has been treated using the refilled blood as the coupling medium.

The next size down from 0.035 inch which is commonly used is a 0.031 inch guidewire. These are generally 180 centimeters long. An 0.025 inch can also be 165 centimeters long. Its use is substantially the same as described above for the 0.035 inch device except it can reach somewhat more distal arteries and ducts and somewhat smaller diameters. Balloon devices may be introduced over it.

The device of the next typical guidewire size, 0.018 inch, retains its guidewire-like quality and may be passed through an introducer through a coronary guiding catheter, up to the coronary ostium, beyond the coronary ostium into the proximal mid and distal coronary arteries and used to successfully image those portions of the artery. A balloon dilatation catheter may then be passed over the proximal end of the pre-placed device and introduced into the coronary arteries. Imaging with the device can be used to guide the location and the use of the balloon dilatation catheter in the coronary artery.

The next smaller size of this device is 0.014 inch in diameter. At present, this is the smallest size guiding type of guidewire that is commonly used in the coronary arteries. Because of its shaft construction and body construction, the ultrasound imaging device, in this size, is contemplated to give good lateral support and minimum traumatic tip profile. Even smaller sizes are contemplated as feasible.

At these particularly small diameters, transducer 16 is very small, even less than 0.008 inch in diameter in certain instances. One might think this would present particular problems because it is known that the beam shape of a transducer is defined as $D^2/4\lambda$ where D is the maximum diameter of the transducer emitting surface and $\lambda$ is the acoustic wavelength being employed. At very small diameters, using present common ultrasound frequencies, the ultrasonic transducer does not produce a beam as needed for imaging but rather produces a pattern similar to that produced by a point source which is not generally useful in imaging.

However, because of the direct exposure of the transducer (no intervening, relatively thick wall or window), much higher ultrasound frequencies may be employed. The device is connected to a source of frequencies between 30 MHz and 300 MHz. Use of such frequencies, made possible in a practical way by the construction described above, achieves an optimal relationship between the diameter of the device and the wavelength and thus provides a coherent beam useful to obtain images.

Various kinds of drive shafts 12 may be employed. For example, the drive shaft may be made in tubular form of the elastic alloy known as nitinol. The nitinol alloy may be tapered or (i.e., flared) to provide graduated stiffness over the length of the overall device, shaft 12 providing some lateral support to body 10. Alternatively, a solid nitinol shaft may be used.

Alternatively, a dual multifilar drive shaft similar to that described in U.S. Pat. No. 4,951,677 may be employed.

Flare or taper 34 to the shaft as shown in FIG. 1 achieves advantages. In certain cases rotational fidelity of shaft 12 is more fully achieved if the drive shaft starts out with a proximal diameter which is larger than the distal diameter.

Another advantage of having such taper or flare 34 is that the lateral stiffness of body 10 can thus be varied as a function of its position and length. For instance, the body in the proximal portion for its first 40 centimeters or so may be of one diameter, say 0.035 inches, whereas body 10 may taper down in a short transition region and in its distal region, over the remainder of the 115 to 125 centimeters length it may be 0.025 inches or less in diameter.

Use of multiple diameters over the length of the device, either stepped or gradually tapered, with both catheter and guidewire constructions may be used to provide desired degrees of lateral stiffness and trackability essential to achieving access to selected regions of the body.

Depending upon the application and the diameter of the device to be made, several different materials may be selected for fabrication of the elongated body 10. In catheter configurations, body 10 is for instance made of a material such as TEFLON, nylon or urethane or other catheter body materials. It may have embedded a metal shield of either wound or braided construction or it may have a metallized layer to provide electrical shielding. Advantageously, the material of the distal region integral with the remaining portions of the body can be selected only for its desirable catheter properties without need to require it be sonolucent.

In guidewire sizes, to achieve greater desired lateral stiffness of body 10, non-polymeric materials may be employed such as nitinol tubing which can be coated with a suitable antithrombogenic coating or with an outer layer of TEFLON to make the outside surface smooth. Alternatively, the body may consist of metal coils of wire which are overwrapped with layers of mylar or layers of shrunk TEFLON tube or polyethylene tube, again with the advantage that there need be no concern for the sonolucency of the body.

This feature is particularly important in metallic versions where body 10 is made out of e.g. nitinol or stainless steel tube or rod or some other wrapped, wound construction since it is often very difficult to provide acoustic windows through such types of materials.

In another construction, shaft 12 is made of a solid single conductive rod which may be tapered, e.g. of nitinol wire for superior rotational fidelity without taking a set. Such a construction presents the problem of how to obtain the return signal to the imaging console since only one conductive member may be used. This difficulty is overcome by first gold-plating shaft 12 and then overcoating it with a di-electric coating. Then over a portion of its length, for instance 5 to 10 centimeters from the distal end, the di-electric coating is again overcoated with another gold layer which is insulated from the first gold layer.

The transducer semi-conductor is connected to the first gold layer and the signal from it is carried back to the imaging console on the metallic shaft. The transducer return path through the gold or conductive lens 30 is brought back to the outer gold layer where it makes no DC connections to anything except to the cylindrical portion described by the second gold layer. This is capacitively coupled to a metallic layer embedded in body 10 which extends back to signal wires through catheter body 10, thence to the imaging console, to complete a suitable acoustic electrical return path.

A further ultrasound imaging device enables acoustic imaging with devices of the type described combined with features enabling infusing a drug or a clot-dissolving enzyme. This is useful to deliver drug or clot-dissolving enzyme in a region of the body which may be blocked or stenosed or have a lesion that supports thrombus which may be hardened.

Figure 7:
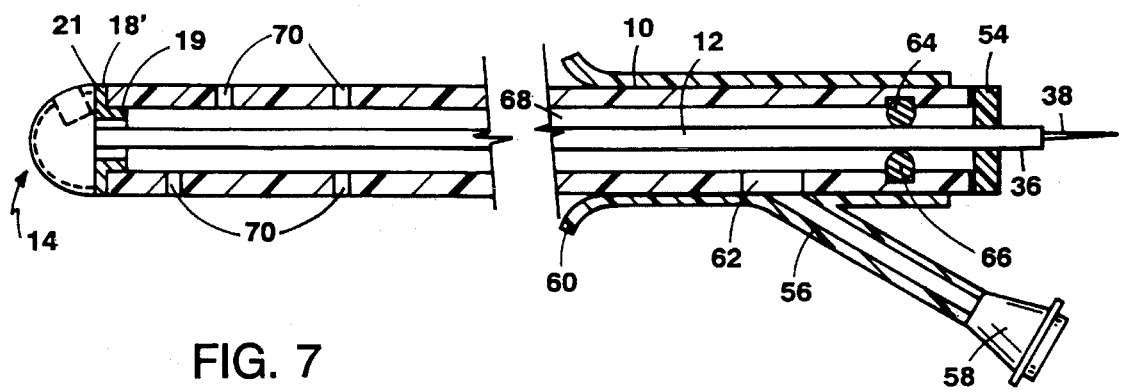
FIG. 7 is a longitudinal cross-sectional view of another ultrasound imaging device which enables combined imaging and fluid infusion or drug delivery.

Referring to FIG. 7, body 10 is provided with a proximal entry side hole 62 which is exposed for alignment with detachable fluid introduction sidearm adaptor 56. Detachable sidearm adaptor 56 is equipped with luer fitting 58, entry flare 60 and a barrel body surrounding body 10.

Entry flare 60 enables the detachable sidearm adaptor 56 to be conveniently slid in position over body 10 while the main barrel portion of the adaptor provides a tight, interfering seal with the exterior surface of body 10 to prevent fluid from escaping from either side of entry port 62. To prevent fluid from migrating proximally inside the body 10, O-ring 64 is disposed in O-ring gland 66 around rotating shaft 12. Luer fitting 58 at the end of detachable sidearm adaptor 56 is adapted to receive an injection syringe to inject fluid under pressure. The fluid enters through proximal side port 62 into the axial passage 68 of the device, between the drive shaft 12 and the internal bore of body 10.

Referring still to FIG. 7, the distal portion of body 10 is provided with infusion holes 70 that communicate with axial passage 68 to enable transfer of fluid from the proximal side hole 62 to the desired region in the patient. Fluid is prevented from substantial leakage at the distal end by thrust bearing 18' disposed between transducer nose assembly 14 and the distal end of body 10. Body 10 is provided with an infusion hole 70 in a selected location or a set of such holes arranged in selected positions and in predetermined number and size to accommodate the desired treatment. These parameters vary with such variables as type of catheter tip, catheter style, size and shape, and type of treatment to be administered.

For instance, discrete focal lesions may be treated by infusion holes which are placed in concentration near the distal end of the catheter. Long distributed lesions may be best treated by placing the infusion holes in a broad and even distribution over a long portion of the body 10.

In FIG. 7, end bearing 18' is comprised of hub portion 19 and flange portion 21. The flange portion of bearing 18' forms a rotating slidable end surface for transducer assembly 14 to bear against endwise when the distal end of the device is pushed against an obstruction. Hub 19 provides a cylindrical bearing surface which resists lateral movement of the shaft and transducer assembly relative to body 10. Together the hub and flange are effective to form a fluid seal and to stabilize the transducer assembly 14, enabling it to withstand lateral and axial forces while still retaining the ability of the assembly to rotate as driven by drive shaft 12.

Figure 9:
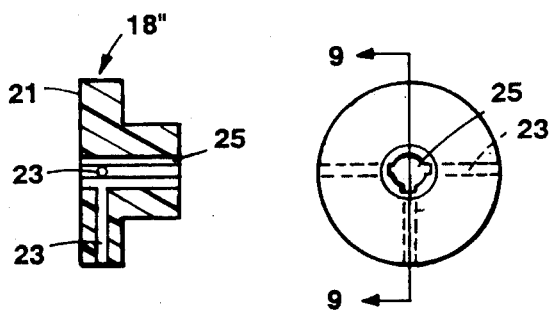
FIG. 9 is a cross-sectional view of the end bearing taken on line 9—9 of FIG. 8.
Figure 8:
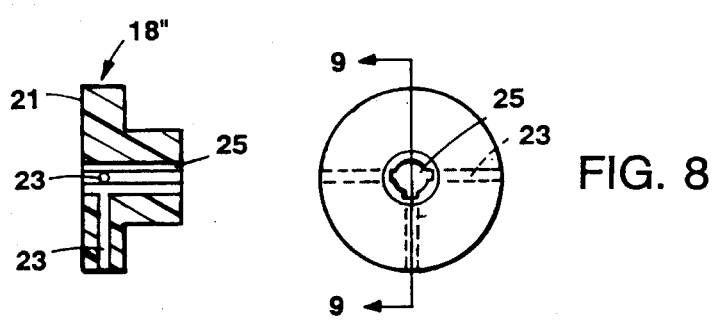
FIG. 8 is an end view of a distal end bearing which enables fluid infusion or drug delivery near the distal tip.

As an alternative to the infusion system based on holes 70 in the body 10, as shown in FIG. 7, FIGS. 8 and 9 show end bearing 18" equipped with radial passages 23 connected to axial passages 25 and outlet port. This construction is effective to enable fluid to pass through end bearing 18" and reach tissue immediately within the field of view of the transducer. The axial passage 25 can be provided by machining a standard woodruff keyway in a bearing member, or the member may be of molded construction formed in other ways. In FIG. 8, three such keyways are shown, one at the bottom and two at the sides. These intersect with drilled radial passages 23 shown in the side view in FIG. 9, at the bottom, and in the end view of FIG. 9 in the center.

Figure 10:
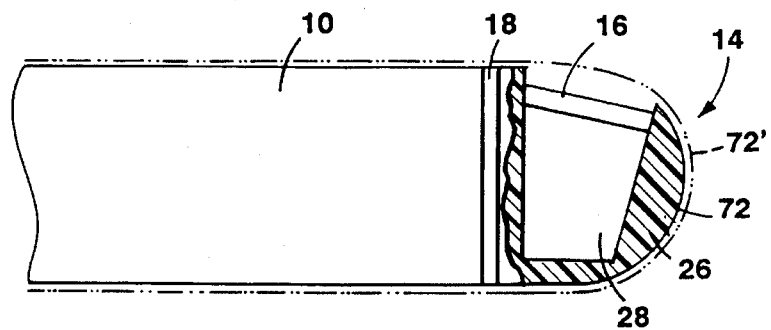
FIG. 10 is a partially cross-sectional view of a catheter or guidewire imaging device covered by a lubricous coating of hydrophilic material.

FIG. 10 shows a catheter or guidewire imaging device having a layer of hydrophilic material 72, formed over transducer assembly 14 as well as over the entire length of the imaging device. FIG. 10 also shows the wetted condition of hydrophilic coating 72', in which the coating has a much greater thickness than it has in its non-wetted condition. The layer of hydrophilic material 72 is in the range of about 40 microns thick, or more, in a wetted condition over transducer assembly 14 and much less thick over the remainder of the catheter or guidewire imaging device.

The hydrophilic coating may be composed of a primer coat and one or more top coats. The primer is composed of an organic solvent and an isocyanate compound such as MDI (methyldifluoroamide) and the top coat or coats are composed of an organic solvent and water-soluble compounds, such as dimethyl formamide and butanol, that form very long chains of hydrocarbons. When wetted, the chains of hydrocarbons remain attached to the surface of the imaging device at their ends and water fills the spaces between the chains by capillary action. Thus, when wetted the hydrophilic coating is comprised mainly of water, which is an ideal material for the transmission of ultrasonic energy and which allows relatively high ultrasound frequencies to be employed. The velocity of the water in the hydrophilic coating tends to decrease with increased distance from the imaging device, due to viscous drag. This particular hydrophilic coating is ablative during rapid rotation of transducer assembly 14, i.e., the hydrophilic coating tends to wear off with time.

The hydrophilic coating can be applied to the catheter or guidewire imaging device by dipping the device in a bath that is a solution of the water-soluble compounds identified above. The entire imaging device is dipped into the bath once to cover the entire imaging device with a single coating, and then transducer assembly 14 is dipped into the bath about 4-6 additional times or more to obtain the requisite thickness.

One suitable coating is available as HYDROPLUS® (Boston Scientific, Watertown, Mass). Alternatively, the coating is gelatin, which is soluble, lubricous when wet, ablative, and acoustically transparent.

The hydrophilic coating shields and spaces rotating transducer assembly 14 from the walls of body passages while providing lubrication. The hydrophilic coating compensates for the lack of a non-rotating sheath surrounding transducer assembly 14.

Figure 11:
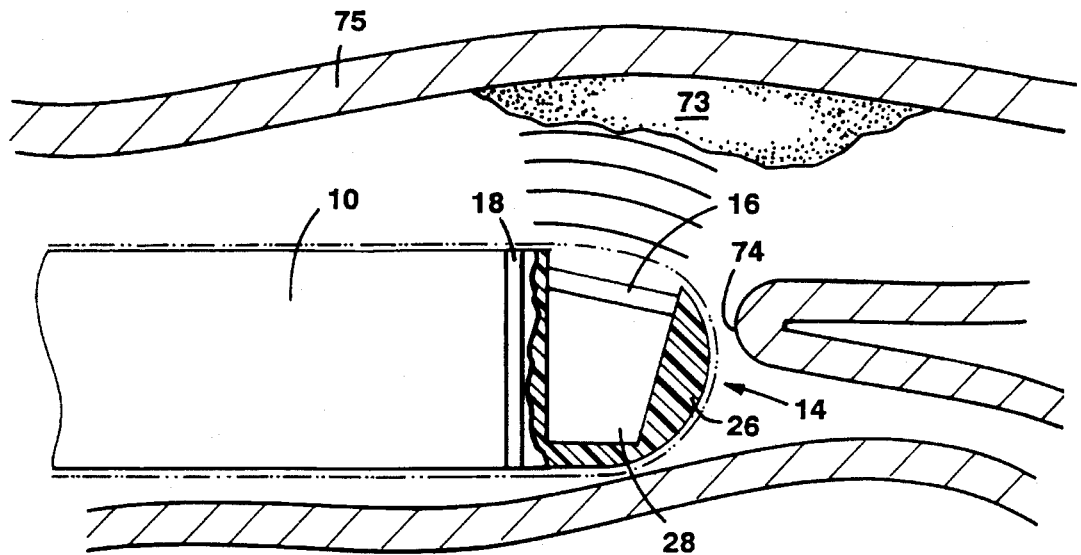
FIG. 11 is a partially cross-sectional view of the catheter or guidewire imaging device of FIG. 10 in use in a patient's blood vessel.

FIG. 11 shows the hydrophilically coated ultrasound imaging device of FIG. 10 operating in a bifurcated artery 75. Coating 72 protects protuberance 74 of artery 75 from the action of the catheter while plaque 73 is imaged. Thus, coating 72 not only helps to avoid abraiding the walls of blood vessels, which is very important because an abrasion in a blood vessel wall could become the site of a thrombosis, but coating 72 is also sufficiently thick to avoid puncturing of the wall of artery 75 at protuberance 74 while transducer assembly 14 rotates sufficiently close to protuberance 74 for puncturing to otherwise occur. Also, hydrophilic coating 72 alleviates tensile forces on the catheter or guidewire imaging device because the presence of the coating makes the device less likely to jam within a blood vessel.

The coating described above in connection with FIGS. 10 and 11 may be applied to catheter or guidewire imaging devices of the type illustrated in FIGS. 7–9. In particular, saline can be injected through holes 70 and radial passages 23 while transducer assembly 14 rotates, in order to create, in effect, an additional protective boundary layer surrounding the coating on transducer assembly 14. This boundary layer is similar to the boundary layer on the wing of an airplane and forms a relatively undisturbed, high-pressure zone that shields transducer assembly 14 from the walls of body passages and also has a lubricating effect. A thrombolytic agent or other drugs can be carried by the injected fluid. Alternatively, the fluid can have a bio-compatible solvent used to dissolve a thrombolytic agent from the inside of the catheter or guidewire imaging device, or from end bearing 18 if the bearing is constructed to be sufficiently porous to hold a relatively large amount of the thrombolytic agent. The coating itself can also contain medications.

There have been described novel and improved apparatus and techniques for medical acoustic imaging. It is evident that those skilled in the art may now make numerous uses and modifications of and departures from the specific embodiments described herein without departing from the inventive concepts.

What is claimed is:

1. An ultrasound imaging device comprising a stationary, elongated flexible tubular body, a rotatable drive shaft extending through said body, and a rotatable nose member located distally of said tubular body, said rotatable nose member being mounted on the distal end of said drive shaft to rotate therewith, and an acoustic imaging instrument incorporated in said rotatable nose member for producing acoustic images of adjacent tissue as said drive shaft turns, said nose member having a rotatable outer surface directly covered with a bio-compatible, lubricous coating of hydrophilic material sufficient to shield and space said outer surface of said nose member from said adjacent tissue as said outer surface rotates with respect to said elongated flexible tubular body, said coating having sufficient thickness to avoid puncturing of a wall of a blood vessel by said nose member while said nose member rotates within said blood vessel sufficiently close to said wall to enable puncturing if said coating were absent.

2. The ultrasound imaging device of claim 1, wherein said lubricous coating comprises an organic solvent and an isocyanate compound.

3. The ultrasound imaging device of claim 2, wherein said isocyanate compound comprises MDI.

4. The ultrasound imaging device of claim 1, wherein said lubricous coating comprises an organic solvent and a water-soluble compound.

5. The ultrasound imaging device of claim 1, wherein said acoustic imaging instrument lies substantially at the surface of said nose member for substantially direct exposure to tissue to be imaged.

6. The ultrasound imaging device of claim 1 wherein said coating covering said rotatable nose member also covers said tubular body over a substantial portion of its length.

7. The ultrasound imaging device of claim 1 wherein said elongated flexible tubular body is a catheter body, said ultrasonic imaging device configured as an intravascular catheter.

8. The ultrasound imaging device of claim 1 wherein said elongated flexible tubular body is sized for use as a guidewire, said ultrasonic imaging device configured as an intravascular guidewire.

9. The ultrasound imaging device of claim 1 wherein said coating of hydrophilic material directly covering said rotatable outer surface of said rotatable nose member erodes from said outer surface during rapid rotation of said nose member.

10. The ultrasound imaging device of claim 1 wherein said coating comprises a medication.

11. The ultrasound imaging device of claim 1 wherein said coating is formed from a solution of said hydrophilic material, and is caused to adhere to said rotatable nose member by dipping said nose member in a bath comprising said solution of said hydrophilic material a sufficient number of times to result in said coating having said sufficient thickness to avoid puncturing said wall of said blood vessel.

12. The ultrasound imaging device of claim 1 wherein said acoustic imaging instrument comprises a transducer.

13. An ultrasound imaging device comprising a stationary, elongated flexible tubular body, a rotatable drive shaft extending through said body, and a nose member located distally of said tubular body, said nose member being mounted on the distal end of said drive shaft to rotate therewith, and an acoustic imaging instrument incorporated in said nose member for producing acoustic images of adjacent tissue as said drive shaft turns, said nose member covered with a bio-compatible, acoustically transparent, lubricous coating of hydrophilic material sufficient to shield and space said nose member from said adjacent tissue, said coating having sufficient thickness to avoid puncturing of a wall of a blood vessel by said nose member while said nose member rotates within said blood vessel sufficiently close to said wall to enable puncturing if said coating were absent, wherein said lubricous coating comprises a primer coat and at least one top coat.

14. An ultrasound imaging device comprising a stationary, elongated flexible tubular body, a rotatable drive shaft extending through said body, and a nose member located distally of said tubular body, said nose member being mounted on the distal end of said drive shaft to rotate therewith, and an acoustic imaging instrument incorporated in said nose member for producing acoustic images of adjacent tissue as said drive shaft turns, said nose member covered with a bio-compatible, acoustically transparent, lubricous coating of hydrophilic material sufficient to shield and space of said nose member from said adjacent tissue, said coating having sufficient thickness to avoid puncturing of a wall of a blood vessel by said nose member while said nose member rotates within said blood vessel sufficiently close to said wall to enable puncturing if said coating were absent, wherein said lubricous coating comprises an organic solvent and a water-soluble compound comprising dimethyl formamide.

15. The ultrasound imaging device comprising a stationary, elongated flexible tubular body, a rotatable drive shaft extending through said body, and a nose member located distally of said tubular body, said nose member being mounted on the distal end of said drive shaft to rotate therewith, and an acoustic imaging instrument incorporated in said nose member for producing acoustic images of adjacent tissue as said drive shaft turns, said nose member covered with a bio-compatible, acoustically transparent, lubricous coating of hydrophilic material sufficient to shield and space said nose member from said adjacent tissue, said coating having sufficient thickness to avoid puncturing of a wall of a blood vessel by said nose member while said nose member rotates within said blood vessel sufficiently close to said wall to enable puncturing if said coating were absent, wherein said lubricous coating comprises an organic solvent and a water-soluble compound comprising butanol.

16. An ultrasound imaging device comprising a stationary, elongated flexible tubular body, a rotatable drive shaft extending through said body, and a nose member located distally of said tubular body, said nose member being mounted on the distal end of said drive shaft to rotate therewith, and an acoustic imaging instrument incorporated in said nose member for producing acoustic images of adjacent tissue as said drive shaft turns, said nose member covered with a bio-compatible, acoustically transparent, lubricous coating of hydrophilic material sufficient to shield and space said nose member from said adjacent tissue, said coating having sufficient thickness to avoid puncturing of a wall of a blood vessel by said nose member While said nose member rotates within said blood vessel sufficiently close to said wall to enable puncturing if said coating were absent and wherein said ultrasound imaging device further comprise a lumen for injection of fluid to create a protective boundary layer surrounding said coating during rotation of said nose member.

17. The ultrasound imaging device of claim 16 further comprising means for providing a drug in said fluid.

18. An ultrasound imaging device comprising a stationary, elongated flexible tubular body, a rotatable drive shaft extending through said body, and an acoustic imaging instrument mounted on said rotatable drive shaft to rotate therewith and to produce acoustic images of adjacent tissue as said drive shaft turns, said ultrasound imaging device being covered over at least a portion of its surface with a bio-compatible, acoustically transparent, lubricous coating of hydrophilic material, said lubricous coating of hydrophic material covering an area of said surface of said ultrasound imaging device through which said acoustic imaging instrument causes acoustic signals to pass, wherein said lubricous coating comprises a primer coat and at least one top coat.

19. The ultrasound imaging device of claim 18, wherein said lubricous coating comprises an organic solvent and an isocyanate compound.

20. The ultrasound imaging device of claim 19, wherein said isocyanate compound comprises MDI.

21. The ultrasound imaging device of claim 18, wherein said lubricous coating comprises an organic solvent and a water-soluble compound.

22. The ultrasound imaging device of claim 18, wherein said acoustic imaging instrument lies substantially at the surface of said ultrasound imaging device for substantially direct exposure to tissue to be imaged.

23. The ultrasound imaging device of claim 18 wherein said coating covers said tubular body over at least substantially all of its length.

24. The ultrasound imaging device of claim 18 wherein said elongated flexible tubular body is a catheter body, said ultrasonic imaging device configured as an intravascular catheter.

25. The ultrasound imaging device of claim 18 wherein said elongated flexible tubular body is sized for use as a guidewire, said ultrasonic imaging device configured as an intravascular guidewire.

26. The ultrasound imaging device of claim 18 wherein said coating of hydrophilic material is ablative during rapid rotation of at least a portion of said ultrasound imaging device.

27. The ultrasound imaging device of claim 18 wherein said coating comprises a medication.

28. The ultrasound imaging device of claim 18 wherein said coating is formed by dipping said ultrasound imaging device in a bath comprising a solution of said hydrophilic material.

29. The ultrasound imaging device of claim 18 wherein said acoustic imaging instrument comprises a transducer.

30. An ultrasound imaging device comprising a stationary, elongated flexible tubular body, a rotatable drive shaft extending through said body, and an acoustic imaging instrument mounted on said rotatable drive shaft to rotate therewith and to produce acoustic images of adjacent tissue as said drive shaft turns, said ultrasound imaging device being covered over at least a portion of its surface with a biocompatible acoustically transparent, lubricous coating of hydrophilic material, said lubricous coating of hydrophic material covering an area of said surface of said ultrasound imaging device through which said acoustic imaging instrument causes acoustic signals to pass wherein said lubricous coating comprises an organic solvent and a water-soluble compound comprising dimethyl formamide.

31. An ultrasound imaging device comprising a stationary, elongated flexible tubular body, a rotatable drive shaft extending through said body, and an acoustic imaging instrument mounted on said rotatable drive shaft to rotate therewith and to produce acoustic images of adjacent tissue as said drive shaft turns, said ultrasound imaging device being covered over at least a portion of its surface with a biocompatible, acoustically transparent, lubricous coating of hydrophilic material, said lubricous coating of hydrophic material covering an area of said surface of said ultrasound imaging device through which said acoustic imaging instrument causes acoustic signals to pass wherein said lubricous coating comprises an organic solvent and a water-soluble compound comprising butanol.

32. An ultrasound imaging device comprising a stationary, elongated flexible tubular body, a rotatable drive shaft extending through said body, and an acoustic imaging instrument mounted on said rotatable drive shaft to rotate therewith and to produce acoustic images of adjacent tissue as said drive shaft turns, said ultrasound imaging device being covered over at least a portion of its surface with a biocompatible, acoustically transparent, lubricous coating of hydrophilic material, said lubricous coating of hydrophic material covering an area of said surface of said ultrasound imaging device through which said acoustic imaging instrument causes acoustic signals to pass and further comprising a lumen for injection of fluid to create a protective boundary layer surrounding said coating during rotation of at least a portion of said ultrasound imaging device.

33. The ultrasound imaging device of claim 32 further comprising means for providing a drug in said fluid.

\* \* \* \* \*